United States Patent
Harding

(10) Patent No.: US 9,775,384 B2
(45) Date of Patent: Oct. 3, 2017

(54) PAIN RELIEVING VEST OR JACKET

(71) Applicant: Marvin Harding, Middle River, MD (US)

(72) Inventor: Marvin Harding, Middle River, MD (US)

(*) Notice: Subject to any disclaimer, the term of this patent is extended or adjusted under 35 U.S.C. 154(b) by 0 days.

(21) Appl. No.: 13/999,262

(22) Filed: Feb. 5, 2014

(65) Prior Publication Data
US 2014/0303532 A1    Oct. 9, 2014

Related U.S. Application Data

(60) Provisional application No. 61/849,940, filed on Feb. 6, 2013.

(51) Int. Cl.
| | |
|---|---|
| *A41D 1/04* | (2006.01) |
| *A61F 5/02* | (2006.01) |
| *A41B 3/02* | (2006.01) |

(52) U.S. Cl.
CPC ............. *A41D 1/04* (2013.01); *A41B 3/02* (2013.01); *A61F 5/026* (2013.01); *A41D 2400/32* (2013.01); *A41D 2400/38* (2013.01)

(58) Field of Classification Search
CPC .. A41D 1/04; A41D 2400/32; A41D 2400/38; A61H 1/008; A41B 3/02; A61F 5/026
See application file for complete search history.

(56) References Cited

U.S. PATENT DOCUMENTS

| | | | | |
|---|---|---|---|---|
| 380,265 | A * | 3/1888 | Lubin ................ | A61F 5/026 2/327 |
| 846,562 | A * | 3/1907 | Grayson ............. | A61F 5/026 2/112 |
| 1,112,201 | A * | 9/1914 | Ersfeld .............. | A61F 5/026 2/267 |
| 1,285,917 | A * | 11/1918 | Bradley ............. | A41D 1/04 2/158 |
| 2,121,168 | A * | 6/1938 | Hibshman .......... | A41D 1/04 2/90 |
| 2,230,798 | A * | 2/1941 | Goldenstein ....... | A41D 1/04 2/90 |
| 2,603,788 | A * | 7/1952 | Page .................. | A41D 1/04 2/106 |

(Continued)

*Primary Examiner* — Sally Haden

(57) ABSTRACT

A pain relieving vest or jacket is an apparatus made of fabric segments having differing material properties comprising of a plurality of longitudinal waves forming a fabric design arranged to provide the vest or jacket with regions of differential compression that applies pressure or support to the neck, shoulder area, chest, sides of the body and back, area to alleviate or prevent pain. With the jacket the arm region is also included. It helps to reduce, alleviate, and the prevention of pain in the neck, shoulder area, chest, sides of the body and back area. The garment has 2 linear strips with hook and loop fastener attachments in the chest area to control and adjust compression. It can be made with or without string or strap attachments in the chest area for additional support to the shoulder area, chest, sides of the body and string or strap attachments for lower back compression. Also the vest does not cover the abdominal area for comfort and convenience to the individual user while wearing the vest.

3 Claims, 1 Drawing Sheet

(56) References Cited

U.S. PATENT DOCUMENTS

Figure 1:
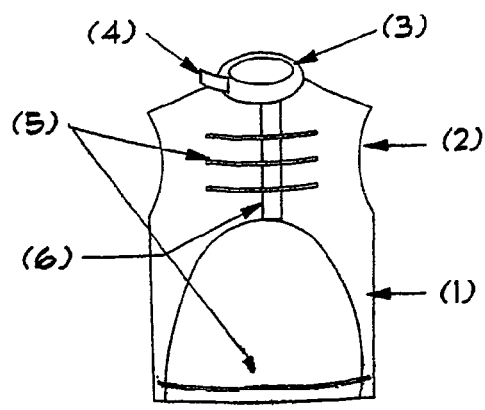

| | | | | |
|---|---|---|---|---|
| 2,642,570 | A * | 6/1953 | Heilbronner | A41D 1/04 2/115 |
| 2,675,556 | A * | 4/1954 | Collier | A41D 1/04 2/108 |
| 4,416,641 | A * | 11/1983 | Spinosa | A41D 13/0125 441/107 |
| 7,028,342 | B1 * | 4/2006 | Nordstrom | A41D 1/04 2/119 |
| 7,117,539 | B1 * | 10/2006 | Baacke | A41D 1/04 2/102 |
| 7,901,371 | B1 * | 3/2011 | Vayntraub | A61F 5/026 602/19 |
| 8,808,212 | B1 * | 8/2014 | Redmond | A61F 5/026 128/846 |
| 2002/0029401 | A1 * | 3/2002 | McEvoy | A41D 19/01582 2/161.7 |
| 2004/0133959 | A1 * | 7/2004 | Horii | A41B 9/06 2/69 |
| 2007/0250984 | A1 * | 11/2007 | Whitmire | A41D 1/04 2/102 |
| 2008/0047044 | A1 * | 2/2008 | Jones | A41D 1/04 2/84 |
| 2009/0095308 | A1 * | 4/2009 | Mckinney | A61F 5/026 128/870 |
| 2009/0265828 | A1 * | 10/2009 | Semba | A41D 1/04 2/69 |
| 2010/0199403 | A1 * | 8/2010 | Greenblat | A41D 1/22 2/69 |
| 2011/0239682 | A1 * | 10/2011 | Raines | A61F 7/10 62/259.3 |
| 2012/0311760 | A1 * | 12/2012 | Puni | A41D 13/0512 2/69 |
| 2014/0059735 | A1 * | 3/2014 | Taylor | A41B 1/08 2/69 |
| 2014/0352026 | A1 * | 12/2014 | Ruth Ann | A41D 27/02 2/69 |
| 2015/0223526 | A1 * | 8/2015 | Nolan | A61H 15/00 2/102 |
| 2015/0272233 | A1 * | 10/2015 | Chen | A41D 1/04 2/113 |
| 2015/0290017 | A1 * | 10/2015 | Taylor | A61F 5/02 602/7 |

\* cited by examiner

PAIN RELIEVING VEST OR JACKET

CROSS-REFERENCE TO RELATED APPLICATION

This application claims the benefits of provisional patent Application No. 61/849,940, filed Feb. 6, 2013

BACKGROUND OF INVENTION

Description of Related Art

There are many devices for the back, shoulder area, chest, and neck pains. Most of these devices are for treatment to specific areas. Examples are back braces, neck braces, and support braces for the shoulder and chest areas. Also there are compression garments.

A neck or back brace is worn for problems that occurred from staying on a computer an extended period of time, sports injuries, car accidents, and other ways that's cause neck problems. And support braces for the shoulder and chest areas are worn for the same type of injuries listed above.

Compression garments which are pieces of clothing are available for specific areas also. FOR EXAMPLE these garments are used to alleviate pain in the neck, chest, back, shoulders, elbow, wrist, and finger pain that have occurred while using a computer possibly, sports injury, car accidents, and other ways that cause pain in those areas.

U.S. Pat. No. 7,901,371 is a posture correcting back brace device for promoting proper posture in the user wearing the device. The device properly corrects the user's posture when he or she is slouching shoulder's forward, and is discrete and comfortable to wear. Two sides of the back plate of the invention are mutually rotatable along a vertical edge which includes a pivot means comprised of a hinge or other device. The back plate further includes a spring means for biasing each side of the back plate away from the user. A pair of shoulder pads each contacts the front side of one of the user's shoulders. The spring means urges each shoulder pad rearward while urging the pivot means of the back plate forward. When the user wearing the invention slouches, the shoulder pads in the invention urge the user's shoulders backwards, thereby correcting the user's posture.

U.S. Pat. No. 4,215,687 relates to body or limb encircling therapeutic devices, and more particularly to a combination of cooperating elements which may be made available preassembled or in kits and utilized to construct such body or limb encircling therapeutic devices on persons suffering from disorders such as lymphedema, phlebitis, varicose veins, post-fracture and injury edema, stasis ulcers, obesity, and circulatory disorders requiring treatment by wearing such therapeutic devices which apply a compressive force on or support of the body or limbs.

U.S. Pat. No. 5,653,244 relates to a therapeutic garment for which is the same principal or type of treatment as present invention. However it is used for leg, ankle, and feet. The garment is made from a flexible, foldable, light weight hook and look type fabric which, due to its inherent characteristics, can be prefabricated in different sizes and need not be custom-made for the wearer. U.S. Pat. No. 6,409,694 is a ventilated neck brace that provides support to the wearer's neck while providing improved ventilation and breathability. Most embodiments of the neck brace are comprised of an elongate member that defines a neck support, a transition section and an elongate shoulder rest. Most configurations of the neck brace allow the wearer to adjust the width and length of the neck brace.

The advantages of my invention is that it will be able to treat the pain or discomfort areas without having to wear two or more different devices. It will treat the back (upper to mid extremities), shoulder area, chest, sides of the body and neck, plus upper and lower arm areas (optional). It can be a vest or a jacket, long or short sleeve, and not only be adjustable by 2 linear fabric strips with hook and loop fastener lining attachment but with polyester string cord or straps that loops or hooks to lock garment in place to make it more efficient for the individual user. Also just as important, it will not bring discomfort to the abdominal area while wearing it, unlike some or maybe most back support devices/compression garments on the market today because the abdominal area is not covered when wearing my garment design.

SUMMARY OF INVENTION

The Pain Relieving Vest or Jacket is a unique invention.

The vest can be worn which will be able to alleviate pain in the neck, shoulder areas, chest, sides of the body, and back area.

The jacket can be worn which will be able to alleviate pain in the neck, shoulder areas, chest, sides of the body, and back area, along with the arm region.

For the pain relieving vest or jacket there is 2 linear strips with hook and loop fastener attachments in the chest area to control and adjust compression in the areas being treated by the garment to the comfort of the individual user. (Neck or collar attachment with hook and loop fastener is optional). Areas of treatment are the shoulders, chest, sides of the body and back (including the trapezius, levator scapulae, infraspinatus, serratus anterior muscle, serratus posterior superior muscle, rhomboid major muscle, teres minor and major muscles, thoracolumbar fascia, and latissimus dorsi muscles). Also the arm region when wearing the jacket. The vest or jacket can be made with or without foam padding, with or without pliable metal stay or sheets in the lower back of the vest. THE GARMENT CAN BE MADE WITH A POLYESTER STRING CORDS OR STRAPS THAT LOOPS OR HOOKS to hold garment in place so garment can apply compression along with OR without the linear strips with hook and loop fastener lining attachment in chest area.

Compression garments are often made of spandex type of material. For example, spandex/polyester, spandex/nylon. Also compression garments can be made of polyester/cotton, nylon/cotton, cotton/bamboo fiber, a therapeutic copper technology, there are many types of material to make the invention. A method of making a compression garment includes combining yarn and/or fibers to form a continuous web that includes plurality of circumferential band regions of differential compression arranged in a predetermined pattern or longitudinal waves corresponding to regions of a user's body. The method also includes forming one or more regions of pile or raised fibers in one or more of the band regions, but not limited to this type of material.

Another method of making a compression garment features combining a plurality of fabrics segments having differing elastic properties to form a compression garment having regions of differential compression, and forming one or more regions of pile or raised fibers in one or more of the fabric segments, but not limited to just this material.

Garments can be also made from a material called Breath-O-Prene™ used for back braces, knee braces, etc. This material helps deliver oxygen back to the skin surface.

AGAIN COMPRESSION GARMENTS CAN BE MADE FROM THE METHODS LISTED ABOVE, BUT NOT LIMITED TO THOSE METHODS DUE TO DIFFERENT AND NEW INNOVATIVE TECHNOLOGIES BEING DEVELOPED AND USED.

Also pliable metal stay or sheets MAY be used just like in back support devices on the market. Also optional, pliable metal stay/sheets or with/without foam padding at the bottom of vest or jacket.

The Garment should be made from a comfortable and flexible material.

The garments should be latex-free if possible for machine washing.

The invention can be made in different colors for consumers to choose from.

Also different size options available for men and women. And the options for kids sizes.

OTHER REFERENCES http://en.wikipedia.org/wiki/Compression_garment
http://en.wikipedia.org/wiki/Back_brace
http://en.wikipedia.org/wiki/Neck_brace

DRAWING FIGURES

FIG. 1. Shows vest frontal view/RIGHT side of invention with 2 linear strips with hook and loop fastener lining starting from lower mid chest area up to collar area, with collar along with a 2 linear strip, hook and loop fastener attachment with foam insulation (optional). Included are 3 polyester string attachments or straps across the chest area. Also vest is shaped from bottom lower right and left sides of body frame, curved lining around the stomach up to beginning of chest area above abdominal area.

Figure 2:
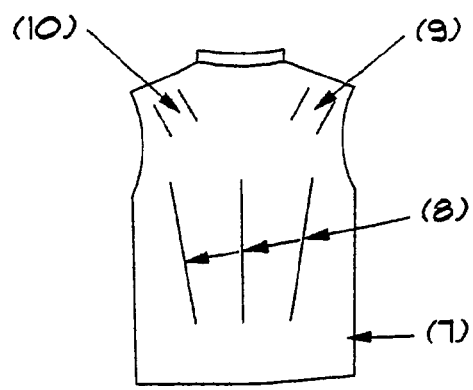

FIG. 2. Shows vest back view of invention

Figure 3:
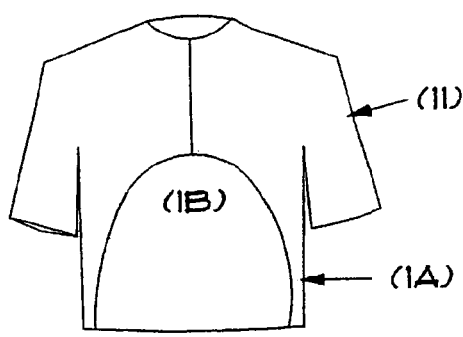

FIG. 3. Shows jacket with frontal view/LEFT side without collar and attachment. Also shows opposite side as it would be under attachment in FIG. 1 of invention with short sleeves made of a compression material.

Figure 4:
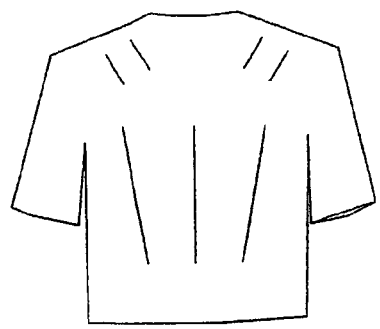

FIG. 4. Shows jacket with back view of invention with short sleeves without a collar, including pliable metal stay or sheets (optional).

Figure 5:
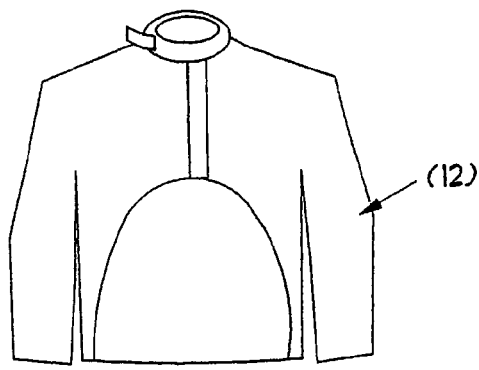

FIG. 5. Shows jacket frontal view of invention with long sleeves and collar with 2 linear strips with hook and loop fastener attachments lining starting from the lower chest area up to collar. Also collar with a 2 linear strip, hook and loop fastener attachment with foam insulation (optional).

Figure 6:
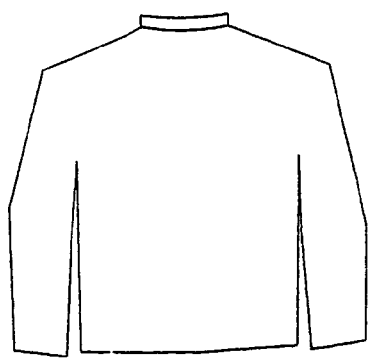

FIG. 6. Shows jacket back view of invention with long sleeves.

DRAWING REFERENCES

1. VEST FRONTAL VIEW/RIGHT SIDE
1 A. VEST FRONTAL VIEW/LEFT SIDE
1B. FRONTAL VIEW OF LINING GOING AROUND THE ABDOMINAL AREA FROM LOWER LEFT TO RIGHT SIDES.
2. No sleeves
3. Collar
4. Adjustable 2 linear strips with hook and loop fastener for collar attachment.
5. Locking polyester 3 string or strap attachments across the chest (Optional).
6. Adjustable 2 linear strips with hook and loop fastener attachment Lining in chest area.
7. VEST BACK VIEW
8. Pliable metal stay or sheets (optional), 8 inches long×½ or so inches wide in lower to midsection of back or vertebrae.
9. Right shoulder area pliable metal stay or sheets (optional) 2 or more inches long×½ inches wide in back of vest.
10. Left shoulder area pliable metal stay or sheets (optional) 2 or more inches long×½ inches wide in back of vest.
11. Short sleeves
12. long Sleeves

DESCRIPTION OF INVENTION

FIG. 1 Shows what the vest looks like from the front. It has 2 linear strips with hook and loop fastener lining up at the beginning of the lower chest area above the abdominal area up to the neck area to adjust to the user's comfort to compress any pain or discomfort in the upper to mid back, along with pain or discomfort in the shoulder, chest, and sides of the body areas. Also there are durable string cord or strap attachments (optional, for example made from polyester) to lock the garment in place for the convenience and comfort of the individual user. Also (optional) there is a collar for neck pains and 2 linear strips with hook and loop fastener attachment to compress that area for pain relief. (((The vest is shaped to go from the lower right and left sides of body frame up to the lower chest and around the abdominal area. THE ABDOMINAL AREA WHEN COMPRESSED CAN BE DISCOMFORTABLE WHILE SITTING, ESPECIALLY AFTER EATING.)))

FIG. 2 Shows what the vest looks like from the back. Within the lower to upper area of the back there are just for illustration 3 pliable metal stay or sheets for the back area for support and 2 pliable metal stay or sheets on the left and right side of the shoulder area for support.

Jackets can be long sleeve or short sleeve depending on the individual choice. Sizes will vary from small, medium, to large and if necessary small for kids and extra large for individuals who require extra large size.

Operation or How Invention Works

The way the Pain Relieving Vest or Jacket works is when either is put on, there is 2 linear strips with hook and loop fastener lining in the front of the chest area for attachment and adjustable to the comfort of the individual user for compression desired. Also there can be a durable string or strap attachments (optional) for attachment and adjustable for the convenience and comfort of the user. The collar (OPTIONAL) with foam insulation along with 2 linear strips with hook and loop fastener attachment to adjust compression in the neck area to the comfort of the individual user if needed. With the jacket it can be long or short sleeves. For long or short sleeves the compression will come from strong, breathable and lightweight compression fabric that feels good to the skin.

The invention claimed is:
1. A compression garment for use by a human user comprising:
   a fabric portion having a neck opening and a waist opening, said neck opening adapted to allow a neck of the user to protrude from said fabric portion,
   said fabric portion having a front adapted to cover a chest of the user, and a back adapted to cover an upper back, shoulders, and a lower back of the user,
   said front having a substantially parabolic opening extending from said waist opening, said substantially parabolic opening terminating at said waist opening and adapted to leave an abdomen of the user uncovered by said front, said substantially parabolic opening having a vertex adapted to be positioned near a sternum of the user, said substantially parabolic opening having a width at said vertex and a width at said waist opening, where said width at said waist opening is greater than said width at said vertex, said front having a vertical opening extending from said neck opening to said vertex, said vertical opening dividing said front into a front left and a front right, said vertical opening having hook and loop fasteners adapted to close selectively attach said front right to said front left and said hook and loop fasteners adapted to selectively open and close said vertical opening, said front having a plurality of parallel horizontal strings extending over said vertical opening on said front from said front left to said front right, said back having a plurality of stays, said plurality of stays including a plurality of shoulder stays adapted to be positioned from a scapula of the user to a collar bone of the user, and a plurality of lower back stays extending substantially vertically and adapted to be positioned on the lower back of the user to support the lower back of the user, said compression garment being adapted to provide effective therapeutic compression, said compression garment being adapted to provide compressive force to the shoulders, the chest, sides, the upper back and the lower back of the user.

2. The compression garment according to claim 1, wherein said compression garment is a jacket with sleeves.

3. The compression garment according to claim 1 wherein said compression garment is a sleeveless vest.

* * * * *